United States Patent [19]

Orchard et al.

[11] Patent Number: 5,817,777
[45] Date of Patent: *Oct. 6, 1998

[54] SUBSTITUTED CYCLOPENTANE COMPOUNDS FOR USE AS CHELATING AGENTS

[75] Inventors: Pamela Joan Orchard, Watlington, United Kingdom; Stephen Randolph Cooper, St. Louis, Mo.

[73] Assignee: Amersham International plc, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 433,503

[22] PCT Filed: Nov. 12, 1993

[86] PCT No.: PCT/GB93/02335

§ 371 Date: May 12, 1995

§ 102(e) Date: May 12, 1995

[87] PCT Pub. No.: WO94/11339

PCT Pub. Date: May 26, 1994

[30] Foreign Application Priority Data

Nov. 13, 1992 [EP] European Pat. Off. .............. 92310367

[51] Int. Cl.$^6$ ....................................................... C07F 5/00
[52] U.S. Cl. ................................ 534/15; 534/16; 424/9.1; 424/9.3
[58] Field of Search ........................ 534/15, 16; 558/432; 562/503, 504; 424/1.11, 9.1, 9.3

[56] References Cited

U.S. PATENT DOCUMENTS 3,507,894  4/1970  Van Volkenburgh ................... 260/439
3,641,149  2/1972  Edgerton ................................. 260/563
3,723,526  3/1973  Edgerton ................................. 260/563
4,088,821  5/1978  Caton et al. ............................. 560/121
4,493,909  1/1985  Haas et al. ............................... 521/166
5,264,606  11/1993 Moloy et al. ............................ 556/482

FOREIGN PATENT DOCUMENTS 1447835  6/1966  France .

OTHER PUBLICATIONS

Seitz et al., *Arch. Pharm.*, vol. 309 (11), pp. 930–932, 1976.

*Primary Examiner*—Gary E. Hollinden
*Assistant Examiner*—Dameron Jones
*Attorney, Agent, or Firm*—Wenderoth, Lind & Ponack

[57] ABSTRACT

The invention provides as new compounds cis-xis-cis-tetrasubstituted cyclopentane compounds which are expected to be useful as chelating agents for alkaline earths, transition, lanthanide, and actinide metal ions. The compounds have Formula (I). Each of the groups $X^1$, $X^2$, $X^3$, and $X^4$ comprises at least one potential ligand donor group, or one of the groups X or Z may comprise a group which may permit attachment to a biological active molecule or insoluble support.

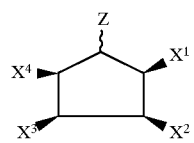

Formula (I)

11 Claims, 6 Drawing Sheets

SUBSTITUTED CYCLOPENTANE COMPOUNDS FOR USE AS CHELATING AGENTS

This invention concerns new substituted cyclopentane compounds which are expected to be useful as chelating agents for alkaline earth, transition, lanthanide and actinide metal ions. Calcium plays a central role in physiological regulatory systems which engenders a need for chelating agents to sequester Ca(II) or to serve as the basis for Ca(II) assays (in, e.g. ion-selective electrodes). Sequestration of other alkaline earths is important for removal of, e.g. $^{90}$Sr. Lanthanide metal ions, especially gadolinium (III), are finding growing use as contrast enhancement agents in magnetic resonance imaging in medicine, for which purpose they must be chelated (e.g. by diethylenetriaminepentaacetic acid, DTPA) to reduce their toxicity. Requirements for actinide chelators arise from fuel reprocessing, actinide decorporation, and effluent treatment.

The compound cis,cis,cis-1,2,3,4-cyclopentanetetracarboxylic acid[1] has been known for many years. Tetraamides of this acid, and some tetraamines formed by reduction of the corresponding tetraamide, are described in U.S. Pat. Nos. 3,723,526[2], 3,641,149 and 3,507,894[3] and in French Patent 1447835[4]. U.S. Pat. No. 4,493,909[5] describes tetraamides of this acid where each amide nitrogen has 2 mono- or bis-(hydroxyl)alkyl substituents as cell-opening components for polyurethane foams.

The compounds all-cis cyclopentane tetra[6]- and pentamethanol[7] and their corresponding mesylate[8] or tosylate [6,9] esters have been described.

The invention concerns new tetrapodal preferably octadentate ligands uniquely suited stereochemically for co-ordination to alkaline earths, transition metals, lanthanides and actinides. The ligands are based upon a cis,cis,cis-1,2,3,4-tetrasubstituted cyclopentane framework.

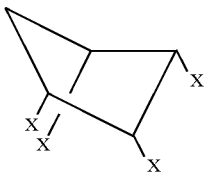

The invention provides substituted cyclopentane compounds of the formula

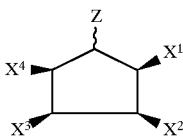

wherein the groups $X^1$, $X^2$, $X^3$ and $X^4$ may be the same or different and each is —CONRR$^1$, —CH$_2$NHCOR, —CH$_2$OCOR, —CH$_2$OR$^1$, —CH$_2$SR$^1$, —CH$_2$SOR, —CH$_2$SO$_2$R or —CH$_2$SO$_2$NRR$^1$, the groups R may be the same or different and each is a C1–C12 hydrocarbon which may optionally be substituted with a potential ligand donor group or a group which may permit attachment to a biologically active molecule or insoluble support R$^1$ is H or R, Z is hydrogen, C1–C20 hydrocarbon which may optionally be substituted with a group which may permit attachment to a biologically active molecule or insoluble support provided that when each of $X^1$, $X^2$, $X^3$ and $X^4$ is CH$_2$OR$^1$, then R$^1$ includes a potential ligand donor group, and provided that, when each of $X^1$, $X^2$, $X^3$ and $X^4$ is —CONRR$^1$, then R and R' are not both mono- or di-hydroxyalkyl and Z is not H.

The stereochemistry of z is undefined. The invention includes such compounds which are attached through Z or a group R to a biologically active molecule or insoluble support. The invention also includes complexes of such compounds with alkaline earth or transition or lanthanide or actinide metal ions.

Groups which may permit attachment to a biologically active molecule or insoluble support include alkyl or aryl amine, carboxyl, isothiocyanate, active ester and others well known in the art.

Potential ligand donor groups include those derived from O—, N—, or S-containing heterocycles, thiols, thioethers, ethers, amines, alcohols, ketones, nitrites or carboxylic, phosphonic, phosphinic, boronic, sulphonic, arsonic or arsinic acids, and their amides and esters, β-diketones, Schiff bases of either ketones, α-diketones or aldehydes, α-hydroxycarboxylic acids, α-ketocarboxylic acids and hydroxamic acids.

One class of ligands results from reaction of esters of cis,cis,cis-1,2,3,4-cyclopentanetetracarboxylic acid (X=COOH) with primary or secondary amines RR—NH where R=H or alkyl, and R includes another potential ligand donor group.

Another class results from reaction of cis,cis,cis-1,2,3,4-tetrakis-(aminomethyl) cyclopentane. (X=CH$_2$NH$_2$) or cis,cis,cis-1,2,3,4-tetrakis(hydroxymethyl)cyclopentane (X=CH$_2$OH) with electrophiles derived from alkyl or aryl groups (which may or may not themselves contain another potential ligand donor group, as specified above), including but not limited to esters, acid chlorides, and anhydrides of carboxylic, phosphinic, phosphinic, arsonic, arsinic acids, unsaturated electrophiles (Michael substrates) e.g. activated olefins such as acrylonitrile, aldehydes, ketones, halides, p-toluenesulphonates, trifluoromethanesulphonates.

Another class results from reaction of the tetraalkyl- or arylsulphonates of cis,cis,cis-1,2,3,4-tetrakis(hydroxymethyl)cyclopentane (X=CH$_2$OH) with nucleophiles derived from alkyl or aryl groups (which may or may not themselves contain another potential ligand donor group, as specified above), including but not limited to amines, thiols or thiolate anions, carboxylic, phosphinic, phosphonic, arsonic or arsinic acids.

Synthesis of Ligands

Figure 1:
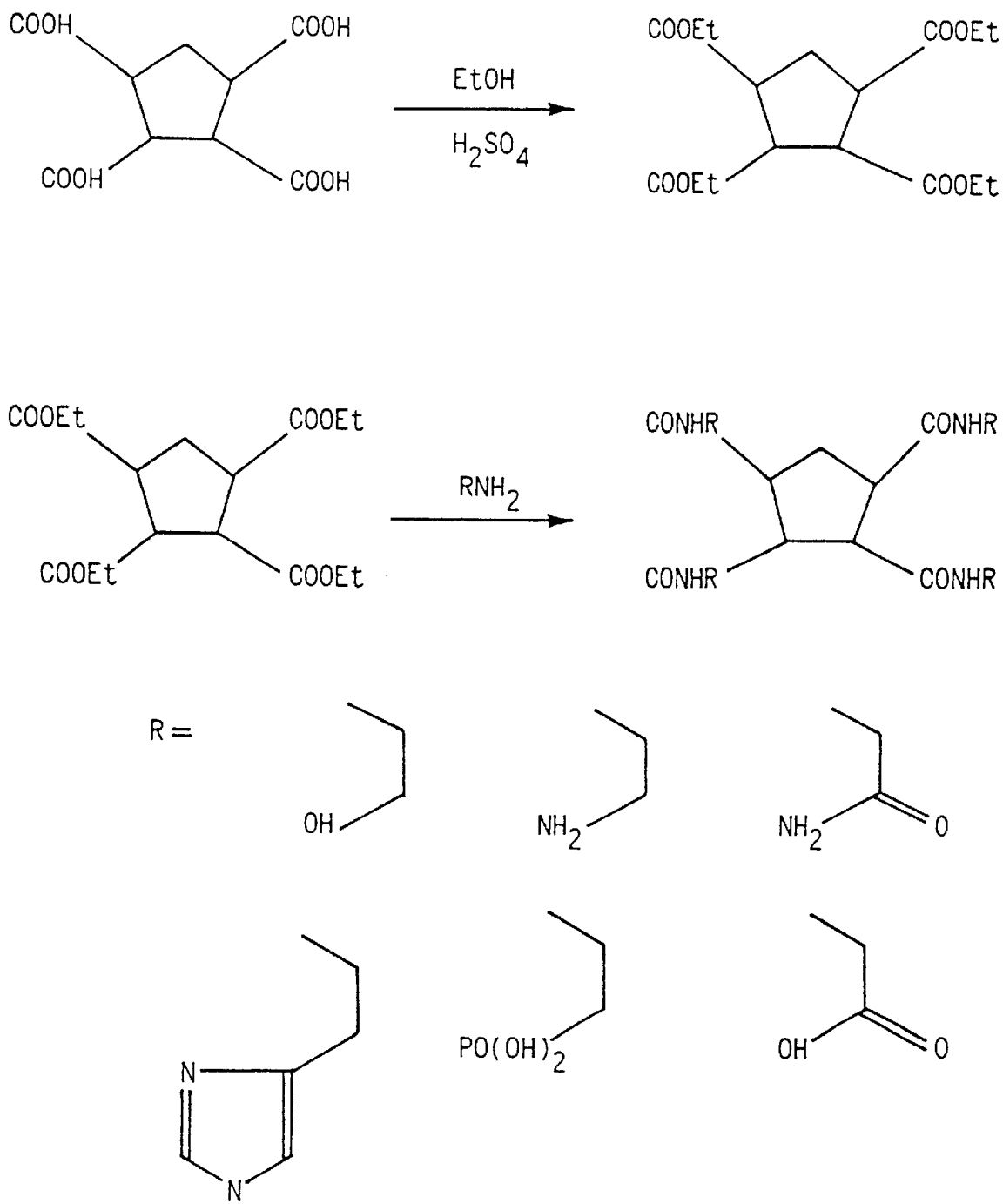
FIG. 1: Tetraamides result from the reaction of the tetraester with an excess of the appropriate primary amine.
Figure 2:
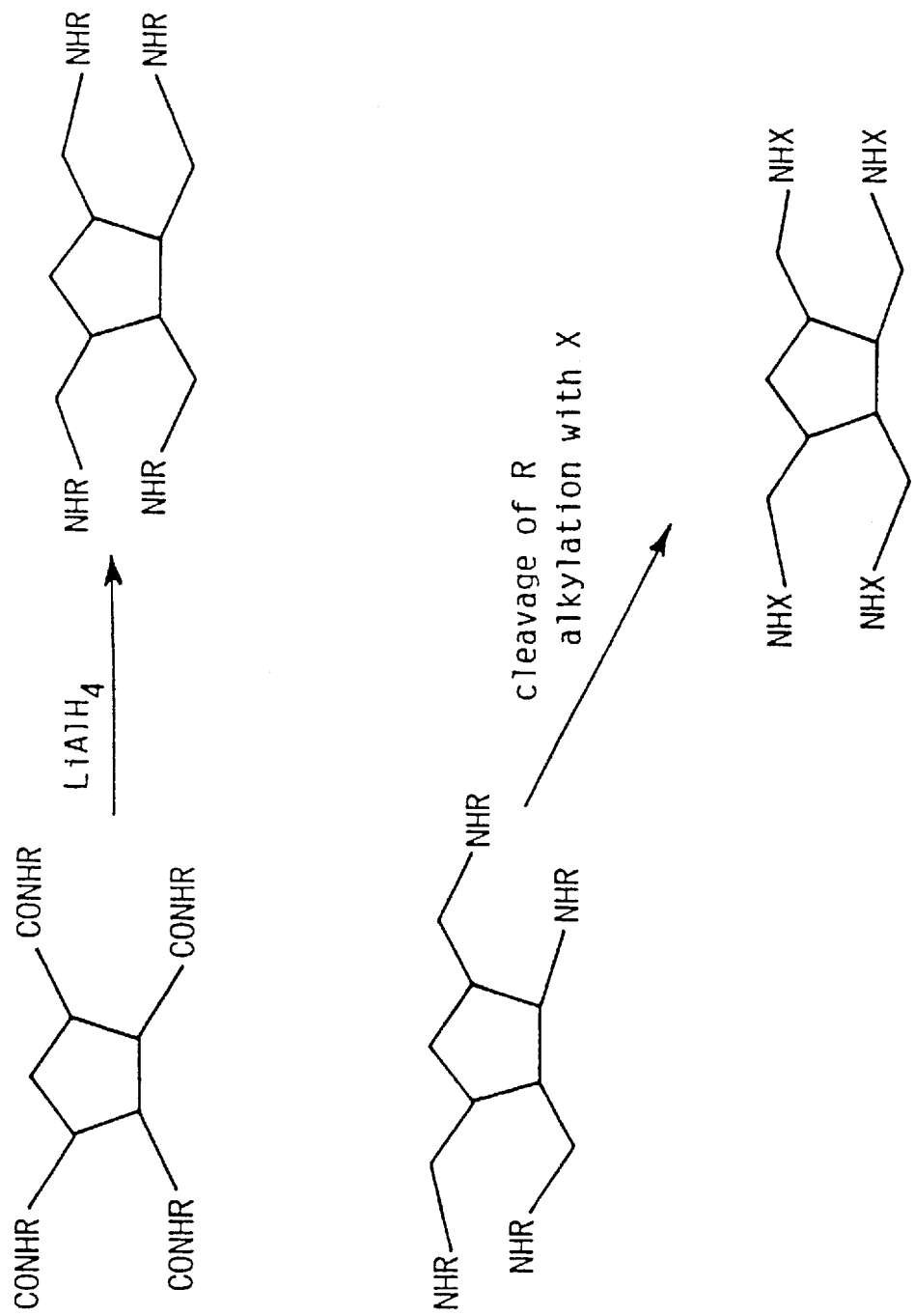
FIG. 2: Reduction of the tetraamide compound yields the tetraamine.
Figure 3:
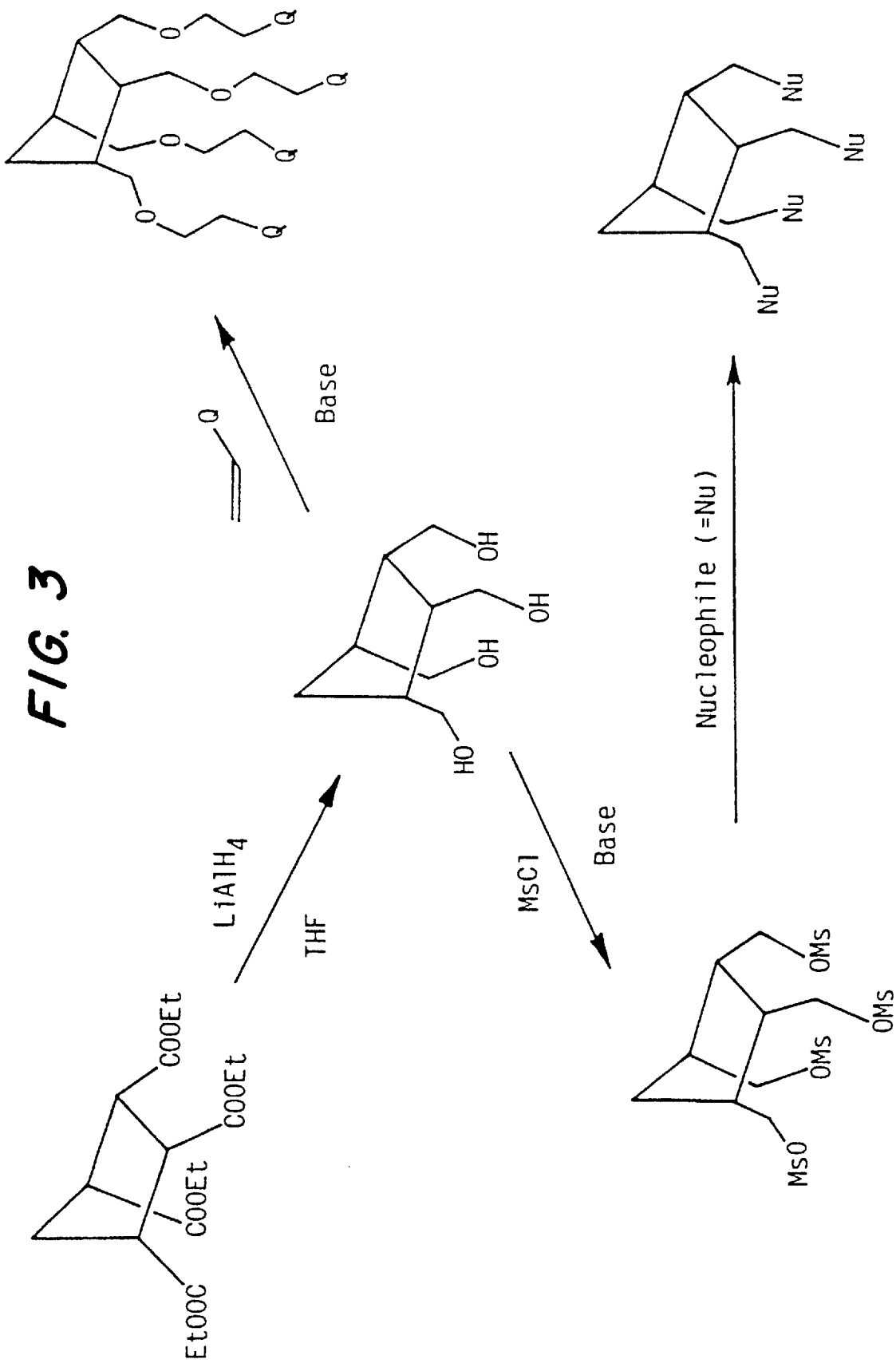
FIG. 3: Reduction of the tetraester to corresponding tetrol and mesylation.
Figure 4:
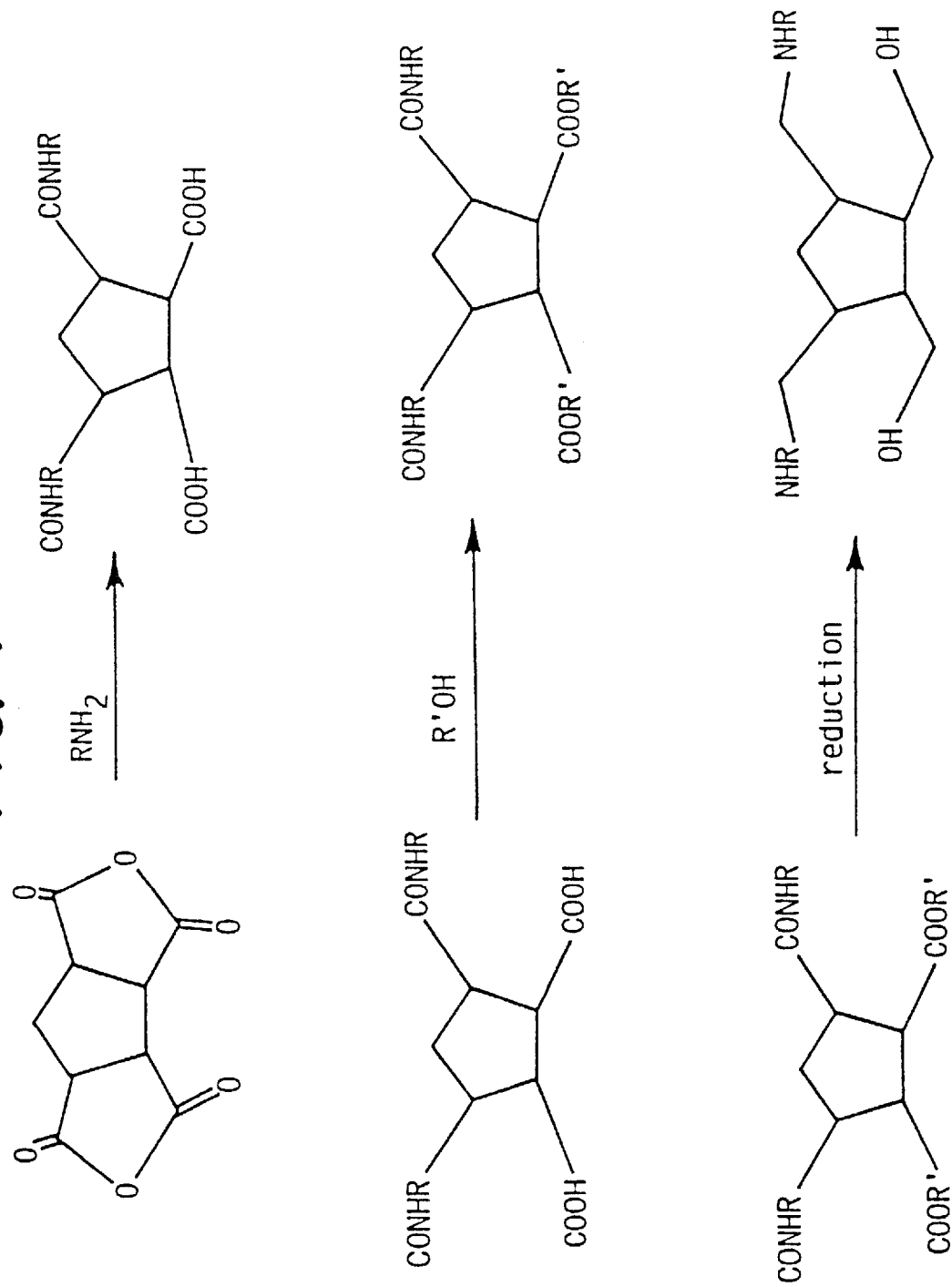
FIG. 4: Ligands with different substituents on cis sites can be obtained by reaction of the dianhydride with a nucleophilic species.
Figure 5:
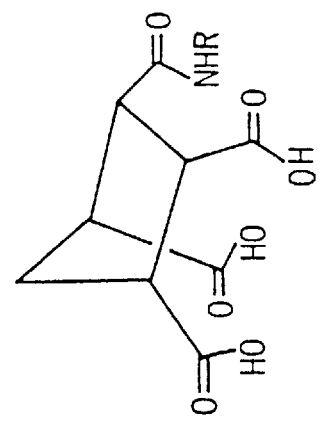
FIG. 5: Ligands with one unique substituent can be obtained by reaction of cis-5 norbornene-endo-2,3-dicarboxylic anhydride.
Figure 5:
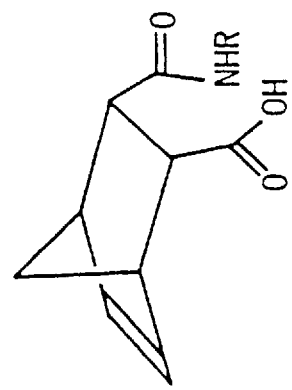
Figure 5:
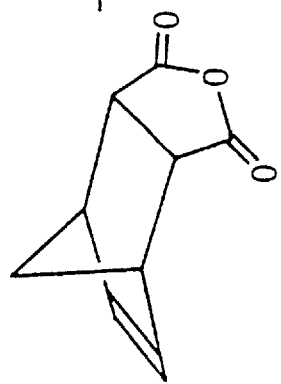
Figure 6:
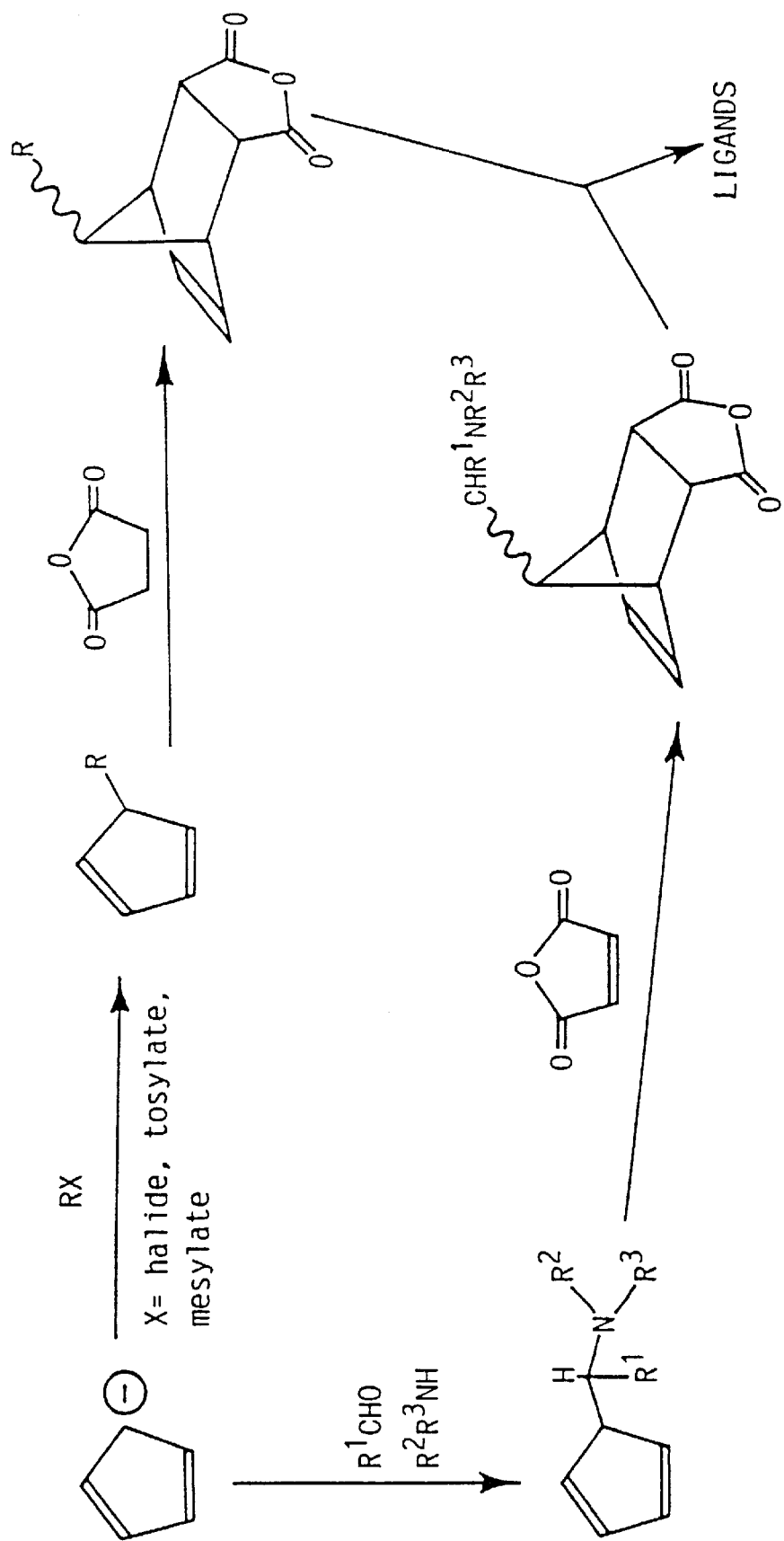
FIG. 6: Substituents can be introduced at the unsubstituted fifth site on the cyclopentane ring.

The known parent compound cis,cis,cis-1,2,3,4-cyclopentanetetracarboxylic acid (X=COOH) is obtained by the hydrolysis of the cis,cis-1,2,3,4-cyclopentane tetracarboxylic dianhydride, or alternatively by Diels-Alder cyclisation of cyclopentadiene with maleic anhydride and oxidation with $KMnO_4$ of the resulting cis-4,5-endonorbornene-2:3-anhydride 3. Conversion of the tetracarboxylic acid to the tetraester is achieved by refluxing the acid in the appropriate alcohol in the presence of a catalytic amount of sulphuric acid[10].

Tetraamides result from reaction of the tetraester (X=COOR) with an excess of the appropriate primary amine (Scheme 1). Several amides with varying substituents have been prepared. Reduction of the tetraamide compound (X=CONH$_2$) gives the tetraamine (X=CHNH$_2$), which allows the preparation of a new group of ligands with N-substituted functionalities (Scheme 2).

In addition, reduction of the tetraester to the corresponding tetrol[10] (X=CH$_2$OH) and mesylation (X=CH$_2$OSO$_2$CH$_3$) provides a route for synthesis of a variety of other ligands (Scheme 3) by nucleophilic substitution. As well, the tetraol may be used to perform Michael addition reactions with unsaturated electrophiles such as acrylonitrile or other activated olefins to give ether linked ligands (Scheme 3).

Ligands with different substituents on two cis sites can be obtained by reaction of the 1:2, 2:3-dianhydride of X=COOH (Scheme 4) with the nucleophilic species cited above. Ligands with one unique substituent can be obtained by reaction of cis-5-norbornene-endo-2,3-dicarboxylic anhydride with a nucleophile followed by oxidation of the double bond (Scheme 5).

Substituents can be introduced at the unsubstituted fifth site on the cyclopentane ring. Alkylation of cyclopentadiene (e.g. by treatment of the sodium salt with halide, tosylate or mesylate, or with aldehyde and an amine, the Mannich reaction) allow introduction of a substituent for possible attachment to, e.g. a monoclonal antibody, protein, nucleic acid, or polymeric support.

Alternatively, one (or two or three) of the groups X may be adapted to permit attachment to a biologically active molecule or insoluble support. For example, one (or two or three) of the groups X may be an amide, with the remainder being non-amide groups.

Coordination of metal ions by multidentate chelating ligands is well known in the literature[11-17]. For one skilled in the art the preparation of such chelate complexes from the ligands claimed here is a straightforward process.

Complexes with radioactive species are of special interest, including $^{165}$Dy, $^{59}$Fe, $^{153}$Sm, $^{156}$Sm, $^{175}$Yb and particularly $^{90}$Y, $^{111}$In, $^{186}$Re, $^{67}$Ga and $^{188}$Re.

The 5-functionalised cyclopentane tetracarboxylic acids can be prepared easily by using functionalised cyclopentadienyl reagents in the initial Diel-Alder condensation used to form the norbornane intermediate in the synthesis of cyclopentane tetracarboxylic acid[18,19]. In this way, bifunctional chelates can be prepared for use in protein or antibody labelling using these ligands.

Experimental Section

EXAMPLE 1
Preparation of all cis-1,2,3,4-cyclopentanetetracarboxylic acid[20]—Compound 1

A suspension of all cis-1,2,3,4-cyclopentanetetracarboxylic acid dianhydride (10.0g, 47.6 mmol) in conc.HCl (100 ml) was heated to 70°–80° C. Ethanol (3 ml) and conc.HCl (50 ml) were added after 1.5 h. When all the starting material had dissolved, heating was discontinued. The mixture was allowed to cool to room temperature and was then evaporated to dryness. Ethyl acetate was added to the residue and the white solid was collected by filtration. This was washed with ethyl acetate and dried under vacuum.

Yield: 10.6 g (90%),
mp. 191°–192° C. [Lit. 192°–195° C.[20]].
$\delta_H$ (D$_2$O) 3.40 (2H,m, —CH—), 3.14 (2H,m, —CH—), 2.27 (2H,m, —CH$_2$—).
$\nu_{max}$ (KBr disc, cm$^{-1}$) 3201 (s,broad), 1744 (s), 1718(s), 1671(s).

EXAMPLE 2
Preparation of all cis-1,2,3,4-tetra(carboethoxy) cyclopentane—Compound 2

All cis-1,2,3,4-cyclopentanetetracarboxylic acid (Cmpd.1, 12.33 g, 50 mmol) was dissolved in ethanol (120 ml) with heating. Conc. H$_2$SO$_4$ (1.2 ml) was added. The mixture was heated under reflux for 40 h and was then allowed to cool. The ethanol was evaporated off. The viscous residue was taken up in ether. The ether solution was washed with water, 5% NaHCO$_3$ solution and brine and was then dried over MgSO$_4$. After filtration of the drying agent the solvent was evaporated off to leave a colourless oil (16.23 g, 90%). The crude material was analysed by HPLC on a NOVAPAK™ C18 column. Solvent A:water, Solvent B:Acetonitrile. Gradient 0–50% B over 25 min, then 50–100% B over 10 min and 100% B for 10 min.=215 nm.

$\delta_C$ (CDCl$_3$) 13.91, 13.99 (CH$_3$), 29.95 (CH$_2$ ring), 45.30, 48.29 (CH ring), 60.67 (CH$_2$ ester), 170.7, 171.66 (C=O).
$\delta_H$ (CDCl$_3$) 1.25 (12H, 2 overlapping triplets, —CH$_3$), 2.35 (1H, dt, —CH$_a$H$_b$-(ring)), 2.77 (1H,dt,—CH$_a$H$_b$-(ring)), ca. 3.10 (2H,m,—CHCO$_2$Et), ca. 3.40 (2H,m,—CHCO$_2$Et), 4.10 (8H,2 overlapping quartets, —CH$_2$CH$_3$).

EXAMPLE 3
Preparation of all cis-1,2,3,4-tetra(carbomethoxy) cyclopentane—Compound 3

All cis-1,2,3,4-cyclopentanetetracarboxylic acid dianhydride (15 g, 71.4 mmol) was suspended in methanol (150 ml). The mixture was heated under reflux for 48 h. Water was added and most of the solvent was removed by rotary evaporation. The product was then extracted into ether. The solvent was removed and the residue was crystallised from a water-methanol (1:4) mixture. White crystals were obtained (12 g, 56%) m.p. 74°–75° C. $\nu_{max}$ (KBr disc, cm$^{-1}$) 3420(b), 1746 (s,CO).

EXAMPLE 4
Preparation of 1,2,3,4-cyclopentanetetrabenzylamide—Compound 4

1,2,3,4-Tetra(carbomethoxy)cyclopentane (Cmpd. 3, 5.0 g, 16.5 mmol) was heated under reflux in excess benzylamine (50 g, 467 mmol). The starting material dissolved to give a clear solution. After 1.5 h a white solid began to precipitate out. The heat source was removed and ethanol was added. The product was filtered off quickly to give the tetrasubstituted product in 20–30% yield. M.p. 262°–266° C.

$\nu_{max}$ (KBr disc, cm$^{-1}$) 3279(s), 1651, 1543.
$\delta_H$(DMSO) 2.1–2.25 (1H, m, —CH$_A$H$_B$-ring), 2.90–3.05 (1H,m, —CH$_A$H$_B$-ring), 3.1–3.3(2H,m,—CH-ring), 3.5–3.65 (2H,m,—CH-ring), 4.0–4.48(8H,m,CH$_2$Ph), 7.1–7.4 (20H,m,-aromatics), 8.10(1H,t,—NH), 8.35 and 8.50 each (1H,m—NH)
MH$^+$ 603
From the filtrate two further compounds were isolated by fractional crystallisation.

Compound 1—Diamide-monoimide[21]
M.p. 192°–198° C.
$\nu_{max}$ KBr disc, cm$^{-1}$ 1774, 1708 (imide C=O), 1643 (amide C=O).
$\delta_H$ (DMSO) 1.95–2.05 (1H,m, —CH$_A$ H$_B$-ring), 2.30–2.45 (1H,m, —CH$_A$H$_B$-ring), 3.05–3.15 (1H,dd,— CH—), 3.20—3.30 (1H,dd, —CH—) 3.40–3.50 (1H,m, —CH—), 3.55–3.60 (1H,m, —CH—), 4.15–4.40 (4H,m, —CH$_2$Ph) 4.5 (2H,s,—CH$_2$Ph, 7.2–7.35 (15H,m, aromatics), ca. 8.5 (1H,m,NH), ca. 8.6 (1H,m,NH).
Compound 2—Diimide
M.p. 149°–150° C.
$\nu_{max}$ (KBr disc, cm$^{-1}$) 1722, 1711 (imide C=O).

EXAMPLE 5
Preparation of 1,2,3,4-cyclopentanetetra (allyl benzylamide) —Compound 5

Allyl chloride (0.85 ml, 10.4 mmol) in benzene (3 ml) was added dropwise with vigorous stirring to a refluxing mixture of the tetrabenzylamide (Cmpd. 4, 1.0 g, 1.66 mmol), finely powdered sodium hydroxide (0.93 g, 23 mmol), potassium carbonate (1.83 g, 13.2 mmol), tetra n-butyl-ammonium-hydrogensulphate (0.077 g, 0.23 mmol) and benzene (10 ml). The mixture was heated under reflux for 4 h. A further aliquot of allyl chloride (0.8 ml, 9.8 mmol) in benzene (1 ml) was added and reflux was continued overnight. The mixture was diluted with toluene and washed with water. The aqueous phase was neutralised with conc. HCl and was extracted with dichloromethane. The toluene and dichloromethane extracts were combined and were washed with brine and dried over Na$_2$SO$_4$. The drying agent was removed and the solvent was evaporated off to give a cloudy oil. The crude material was chromatograped on silica gel using ether:hexane (1:1) and then (2:1) as eluant. The fractions which were isolated were purified further by HPLC on a Hichrom™ reverse phase column (HiRBP-2500 ISP). Solvent A—Water, Solvent B—Acetonitrile. Gradient: 0–80% B over 30 min. Two pure compounds were recovered:
Compound 1 -0.16 g MH$^+$: 763
Compound 2 -0.16 g MH$^+$: 763

EXAMPLE 6
Preparation of 1,2,3,4-tetra(hydroxymethyl)cyclopentane[6] —Compound 6

A solution of 1,2,3,4-tetra(carboethoxy)cyclopentane (Cmpd. 2, 10.03 g, 28 mmol) in dry THF (70 ml) was added dropwise over 45 min to a suspension of lithium aluminium hydride (2.15 g, 56.6 mmol) in THF (40 ml). The mixture warmed during the addition and was then heated under reflux overnight. After cooling, water (5 ml) was added and the mixture was allowed to stir at room temperature for several hours. The salts were then filtered off and washed several times with THF. The THF washings were evaporated to give an oil. The salts were extracted with THF in a Soxhlet apparatus over 32 days. The THF was evaporated off and the residue was combined with the oil above. This crude material was chromatographed on silica gel using acetone:ethyl acetate:methanol (5:4:1) as eluant. The fractions containing the major product were combined and evaporated to leave a colourless oil. This was pumped under vacuum to remove traces of solvent.
Yield 4.27 g (80%).
$\delta_H$ (DMSO) 1.05–1.15 (1H,m, —CH$_A$H$_B$-ring), 1.7–1.9 (1H,m, —CH$_A$H$_B$ ring), 2.0–2.25 (4H,m, —CH-ring), 3.3–3.6 (4H,m, —CH$_2$OH) 4.51 (2H,t, J=5.0 Hz,— CH$_2$OH), 4.58 (2H,t, J=4.6 Hz, —CH$_2$OH). Signals at 4.51 and 4.58 disappear on addition of H$_2$O.

EXAMPLE 7
Preparation of 1,2,3,4-tetra(mesyloxymethyl) cyclopentane—Compound 7

A solution of mesyl chloride (2.0 g, 17.6 mmol) in dichloromethane (10 ml) was cooled to 0° C. A solution of 1,2,3,4-tetra(hydroxymethyl)cyclopentane (Cmpd. 6, 0.67 g, 3.5 mmol) in dichloromethane (25 ml) containing DMAP (2.16 g, 17.7 mmol) and triethylamine (1.79 g, 17.7 mmol was added dropwise over 1 h, keeping the temperature at 0° C. The mixture was then stirred at 0° C. for 3 h. A white solid precipitated out. The reaction mixture was washed with 1M HCl, satd. NaHCO$_3$ and brine and was dried over Na$_2$SO$_4$. After filtration of the drying agent and removal of the solvent the crude material was chromatographed on silica gel using dichloromethane:ethyl acetate (2:1) and then (1:1) as eluant. The pure fractions of manor product were combined to give 1.19 g (67%). M(NH$_4^+$) 520. $\delta_H$ (CDCl$_3$) 1.4–1.5 (1H,m, —CH$_A$H$_B$-ring), 2.1–2.2 (1H,m, —CH$_A$H$_B$-ring), 2.6–2.8 (4H,m, —CH-ring), 3.06 (6H,s, —SO$_2$CH$_3$), 3.08 (6H,s, —SO$_2$CH$_3$), 4.2–4.45 (8H,m, —CH$_2$O—).

Two higher running components were isolated in smaller quantities. They appear to be monocyclised products.

Component 1—$\delta_H$ (CDCl$_3$) 1.35–1.45 (1H,m, —CH$_A$H$_B$-ring), 2.05–2.2 (1H,m, —CH$_A$H$_B$-ring), 2.40–2.53 (1H,m, —CH-ring), 2.55–2.65 (1H,m, —CH-ring), 2.73–2.95 (2H, m, —CH-ring), 2.98 (3H,s, —SO$_2$CH$_3$), 3.00 (3H,s, —SO$_2$CH$_3$), 3.38 (1H,dd, J=6.9 Hz and J=9.6 Hz. —CH$_C$H$_D$ -THF ring), 3.53–3.63(2H,m, —CH$_C$H$_D$-THF ring), ca. 3.68 (1H, brd, ca. 9.5 Hz. —CH$_C$H$_B$-THF ring) 4.16–4.32 (2H,m, —CH$_2$OMs).

Component 2—$\delta_H$ (CDCl$_3$) 1.13 (1H,m, —CH$_A$H$_B$—) 1.67 (1H,m, —CH$_A$H$_B$), 2.42–2.56 (2H,m, —CH-ring), 2.88–2.94 (2H,m, —CH-ring), 3.0 (6H,s,SO$_2$CH$_3$), 3.58–3.65 (2H,m, dd, J=11.5 and 9.9 Hz, —CH$_C$H$_D$-THF ring), 3.75 (2H, dd, J=3.0 and J=9.9 Hz, —CH$_C$H$_D$-THF ring), 4.2–4.4 (4H,m, —CH$_2$OMs).

EXAMPLE 8
Preparation of 1,2,3,4-tetra(carbomethoxymethylthiomethyl)cyclopentane—Compound 8

Sodium hydride (60% in oil) (0.24 g, 6 mmol) was washed with hexane and suspended in dry DMF (13 ml) Methyl thioglycolate (540 μl, 6 mmol) was added at −10° C. under a nitrogen atmosphere. Hydrogen gas evolved. The tetramesylate (Cmpd.7, 0.50 g, 1 mmol) in DMF (7 ml) was added dropwise at −10° C. over 1 h. The reaction mixture was stirred at −10° C. for a further 2 h and then at 0° C. for 4 h. It was then allowed to warm to room temperature overnight (total 20 h). The solvent was removed by rotary evaporation. Ethyl acetate was added and this was washed twice with brine. The organic extract was dried over MgSO$_4$ and the solvent was evaporated off. The residue was chromatographed on silica gel using hexane:ethyl acetate (3:1), then (2:1) and (1:1) as eluant. Two manor components were isolated.

Component 1—0.195 g (54%) cyclised product. M(NH$_4^+$) 382. $\nu_{max}$ (liquid film) 1738 cm$^{-1}$. $\delta_H$ (CDCl$_3$) 1.07–1.21 (1H,m, —CH$_A$H$_B$), 1.87–1.95 (1H,m, —CH$_A$H$_B$), 2.1–2.25 (2H,m, —CH-ring), 2.55–2.63 (2H,m, —CH-ring), 2.68 (4H,d, J=7.9 Hz, —SCH$_2$CH), 2.8–2.9 (4H,m, —CHSCH$_2$—), 3.21 (4H,s, —S—CH$_2$CO$_2$Me), 3.7 (6H,s, —CO$_2$CH$_3$).

Component 2—0.162 g (30%) Tetraester. $\nu_{max}$ liquid film) 1736 cm$^{-1}$. $\delta_H$ (CDCl3) 1.15–1.25 (1H,m, —CH$_A$H$_B$—), ca. 2.2–2.35(5H,m, —CH$_A$H$_B$— and CH-ring), 2.43–2.51 (2H,m, —CH$_2$S—), 2.66–2.92 (2H,m, —CH$_2$S—), 3.2–3.3 (8H,m, —SCH$_2$CO$_2$Me), 3.71 and 3.72 (12H, both s, —CO$_2$CH$_3$).

EXAMPLE 9
Preparation of 1,2,3,4-tetra [(o-carbomethoxyphenylthio) methyl]cyclopentane—Compound 9

NaH (240 mg, 60% in oil 6 mmol) was washed with dry n-hexane twice before use and was suspended in dry DMF (14 ml). Methyl thiosalicylate (1.01 g, 6 mmol) was added by syringe under nitrogen at 0° C. Hydrogen gas evolved and the solution colour changed to red. 1,2,3,4-tetra (mesyloxymethyl)cyclopentane (Cmnpd.8, 0.50 g, 1 mmol) in dry DMF (6 ml) was then added dropwise to the reaction mixture at 0° C. The mixture was stirred at 0° C. under nitrogen for 3 h and then gradually heated to room temperature. 100 mL of EtOAc was added to the solution. The organic phase was washed with water twice and brine, and was then dried over anhydrous $MgSO_4$. Purification of the product using silica gel column chromatography eluting with n-hexane/EtOAc (2:13:21:1) gave 510 mg of the corresponding tetraester in 64% yield.

$^1$H NMR (CDCl$_3$); 1.5–1.6 (m, 1H, —CH$_A$—H$_B$—), 1.8–1.9 (m,1H, —CH$_A$H$_B$—), 2.4–2.7 (m, 4H, —CH-ring), 2.8–2.9 (m, 2H, CH$_2$S), 3.1–3.3 (m, 4H, CH$_2$S), 3.4–3.5 (m, 2H, CH$_2$S), 3.67 (s, 6H, COOMe), 3.91 (s, 6H, COOMe), 7.1–7.2 (m, 4H, arom), 7.4–7.6 (m, 8H, arom), 7.93 (dd, 4H, J=7.8, 1.8 Hz, arom) ppm.

EXAMPLE 10
Preparation of 1,2,3,4-tetra(2'-cyanoethoxymethyl) cyclopentane—Compound 10

A 40% aqueous potassium hydroxide solution (0.12 g) was added to 1,2,3,4-tetra(hydroxymethyl)cyclopentane (Cmpd.6, 2.80 g, 14.7 mmol) in p-dioxane (2.5 ml). The mixture was stirred vigorously and acrylonitrile (4.50 ml, 68.5 mmol) was added dropwise. During addition the reaction mixture warmed slightly and was cooled on a waterbath. It was then allowed to stir at 30° C. for 20 h. 2.5M HCl (1.75 ml) was added and the mixture was evaporated to dryness. The residue was purified by flash column chromatography on silica gel using ethyl acetate:hexane (3:2) as eluant and increasing the solvent polarity to 100% ethyl acetate. Two major products were isolated.

Compound 1—5.24 g (88%) Tetranitrile M(NH$_4^+$) 420.

$\nu_{max}$ (liquid film) 2251(s) cm$^{-1}$.

$\delta_H$ (CDCl$_3$) 1.29–1.38 (1H,m, —CH$_A$H$_B$—), 1.9–2.0 (1H, m, —CH$_A$H$_B$—), 2.3–2.47 (4H,m, —CH-ring), 2.55–2.60 (8H,m, —CH$_2$CN), 3.45–3.68 (16H,m, —CH$_2$OCH$_2$—).

$\delta_C$ (CDCl$_3$) 18.7 (CH$_2$-ring), 39.9 (—CH-ring), 42.7 (—CH-ring), 65.3, 65.4, 68.8 and 72.2 (—CH$_2$O—CH$_2$CH$_2$—) 118.1 and 118.2 (—CN).

Compound 2—0.31 g (6%) M(NH$_4^+$) 367 Trinitrile mono-ol.

$\delta_H$ (CDCl$_3$) 1.2–1.35 (1H,m, —CH$_A$H$_B$), 1.75–2.0 (1H,m, —CH$_A$H$_B$—) 2.2–2.9 (10H,m, —CH$_2$CN and —CH-ring), 3.3–3.8 (14H, m, —CH$_2$O—CH$_2$ and CH$_2$OH).

EXAMPLE 11
Preparation of 1,2,3,4-tetra(2'-carbomethoxyethoxymethyl) cyclopentane—Compound 11

The tetranitrile (Cmpd.10, 2.55 g, 6.4 mmol) was dissolved in dry methanol (29 ml) under a nitrogen atmosphere. Dry HCl gas was bubbled into the solution over 20 min. A white precipitate formed and the mixture was heated under reflux for 1 h. It was then allowed to stand at room temperature over the weekend. The white precipitate of NH$_4$Cl was filtered off and washed with benzene. The filtrate was evaporated to leave a brown oil. This was purified on silica gel using hexane/ether (1:1) as eluant and increasing the polarity of the solvent to hexane/ether (2:5). Two major components were isolated.

Component 1—0.93 g. M(NH$_4^+$) 484 (unknown)

$\nu_{max}$ (liquid film) 1741 cm$^{-1}$. $^{13}$C NMR indicates a mixture of compounds $^1$H NMR spectrum consistent with a tetramethyl ester structure Component 2—0.61 g M(NH$_4^+$) 552 (tetramethylester)

$\nu_{max}$ (liquid film) 1741 cm$^{-1}$, $\delta_H$ (CDCl3) 1.05–1.2 (1H,m, —CH$_A$H$_B$), 1.6–2.35 (5H, m, —CH$_A$H$_B$— and —CH-ring), 2.4–2.6 (8H,m, —CH$_2$CO$_2$Me), 3.2–3.8 (28H,m, —CH$_2$OCH$_2$ and CO$_2$CH$_3$).

EXAMPLE 12
Preparation of 1,2,3,4-tetra (2'-carbo-t-butoxyethoxymethyl)cyclopentane—Compound 12

1,2,3,4-tetra (hydroxymethyl)cyclopentane (Cmpd.6, 1.0 g, 5.26 mmol) and dicyclohexyl 18-crown-6 (0.08 g, 0.21 mmol) were dissolved in DMF (4 ml). One drop of 40% KOH was added at room temperature. After addition of t-butyl acrylate (4.6 ml, 31.4 mmol) by syringe, the reaction mixture was stirred overnight. EtOAc (50 ml) was added to the reaction mixture and then the organic phase was washed with brine (30 mL×3) and was dried over MgSO$_4$. The crude material was purified using column chromatography on silica gel eluting with n-hexane/EtOAc (5:2 to 1:1) and gave tetraester (2.66 g, 72%) and triester-mono OH (0.48 g, 16%).

Tetraester; colourless liquid, $^1$H nmr (CDCl$_3$): 1.1–1.3 (m, 1H, —CH$_A$H$_B$—) 1.44 (s, 36H, CH$_3$), 1.8–1.9 (m, 1H, —CH$_A$,H$_B$—), 2.2–2.4 (m, 4H, —CH-ring), 2.46 (t, 8H, CH$_2$CO), 3.3–3.5 (m, 8H, CH$_2$O), 3.60 (t, 4H, OCH$_2$CH$_2$CO) and 3.62 (t, 4H, OCH$_2$CH$_2$CO) ppm; $^{13}$C NMR (CDCl$_2$); 28.1, 33.0, 36.4, 40.1, 42.9, 66.5, 68.6, 72.5, 60.3 and 171.0 ppm. MS (DCI): 720 (M+NH$_3$)

Triester-monoOH (including isomers); colourless liquid, 1H NMR (CDCl$_3$): 1.1–1.3 (m, 1H, —CH$_A$H$_B$), 1.44 (s, 27H, CH$_3$), 1.8–1.9 (m, 1H, —CH$_A$H$_B$) 2.2–2.4 (m, 4H, —CH-ring), 2.46 (m, 6H, CH$_2$CO) and 3.2–3.7 (m, 14H, CH$_2$OCH$_2$ and CH$_2$OH)ppm; $^{13}$C NMR (CDCl$_3$; 28.1, 30.6, 32.1, 36.2, 36.3, 38.9, 39.2, 40.7, 42.3, 42.9, 43.0, 44.1, 46.6, 60.3, 63.6, 66.6, 66.7, 68.7, 72.0, 72.2, 72.6, 80.4, 80.7, 80.8, 170.7 and 170.9 ppm; MS (DCI); 592 (M+NH$_3$).

EXAMPLE 13
Preparation of 1,2,3,4-tetra(2'-carboxyethoxymethyl) cyclopentane—Compound 13

A From tetramethylester (Cmpd. 11)

A mixture of 12% aq. sodium hydroxide (0.75 g), water (3.0 g), THF (3.0 g) and methanol (0.5 g) was added to the tetramethylester (Cmpd.11, 0.20 g, 0.37 mmol). The reaction mixture was stirred at room temperature for 17 h. Not all of the starting material had dissolved so a further amount of THF (1.0 g) was added. The mixture was stirred at room temperature for a further 5 h. The temperature was then increased to 80° C. and kept at this temperature for 2 days. The organic solvents were evaporated off and the aqueous phase was washed with ether. The aqueous phase was then acidified with conc. HCl and the water was removed by rotary evaporation. The solid residue was washed several times with ether. The ether washings were combined and evaporated to give an oil, 0.29 g. IR showed presence of an acid. TLC in [CHCl$_3$:MeOH:AcOH (90:10:1)] showed two manor components. After column chromatography in this system only about half of the material was recovered. Infrared showed presence of an ester.

B From tetranitrile

Conc.HCl (23 ml) was added to the tetranitrile (Cmpd.10, 5.24 g, 13 mmol) and the mixture was heated under reflux for 4 h. The mixture was allowed to cool to room temperature and a white solid precipitated out. This was filtered off. NaOH (~10 g) in H$_2$O was added to the filtrate to bring the pH to 10. The aqueous solution was washed with THF. The pH of the aqueous phase was brought to 1 using conc.HCl, and the aqueous phase was extracted with THF until no further acid could be extracted (as judged by TLC). The THF extracts were evaporated to dryness and the crude material was chromatographed on silica gel using hexane:THF:acetic acid (40:20:1) increasing to (30:30:1). Two manor closely-running components could not be separated. Several attempts were made using flash column chromatography and also dry flash column chromatography, but the mixture could not be separated.

$v_{max}$ (liquid film) 3200–3300 (b), ca. 2500 (b), 1724 cm$^{-1}$ $\delta_H$(CDCl$_3$) 0.8–1.1 (1H,m, —CH$_A$H$_B$—), 1.5–1.7 (1H,m, —CH$_A$H$_B$—), 1.75–1.95 (1H,m, —CH-ring), 1.95–2.1 (1H, m, —CH-ring), 2.2–2.55 (10H,m, —CH-ring and —CH$_2$CO$_2$H), 3.2–3.8 (16H, m, —CH$_2$OCH$_2$—), ca. 8.0 (broad s, —OH).

Peak at ca. 8.0 disappears on addition of D$_2$O.

B From tetra $^t$butyl ester

TFA (4.0 g, 52 mmol) was added to 1,2,3,4-tetra(2'-carbo-t-butoxyethoxymethyl)cyclopentane (Cmpd.12, 1.0 g, 1.42 mmol) in CHCl$_3$ (3 ml) at room temperature. After 2 h the solvent was removed and the product was dried by vacuum pump.

Tetracarboxylic acid; colourless liquid, $^1$H NMR (DMSO-d6): 1.1–1.3 (m, 1H, —CH$_A$H$_B$—), 1.7–1.9 (m, 1H, —CH$_A$H$_B$—), 2.16 (m, 4H, —CH-ring), 2.3–2.5 (m, 8H, CH$_2$CO), 3.2–3.5 (m, 8H, CH$_2$O), 3.5–3.6 (m, 8H, OCH$_2$CH$_2$CO) and 10.01 (brs, 4H, COOH) ppm; $^{13}$C NMR (DMSO-d6): 32.9, 34.9, 42.4, 66.06, 66.12, 67.9, 71.9 and 172.8 ppm, MS (Electrospray): 477 (M—H—).

EXAMPLE 14

Preparation of 1,2,3,4-tetra(allyoxymethyl)cyclopentane—Compound 14

Sodium hydride, 60% in oil (1.65 g, 42 mmol) was washed three times with hexane under a nitrogen atmosphere and was then suspended in dry DMF (10 ml). A solution of 1,2,3,4-tetra(hydroxymethyl)cyclopentane (Cmpd.6, 1.75 g, 9.25 mmol) in DMF (20 ml) was added dropwise at room temperature with stirring. Hydrogen gas evolved. The mixture was stirred at room temperature for 3 h. It was cooled on an ice bath and allyl chloride (4.5 ml, 55 mmol) was added over 45 min. The mixture was then allowed to warm to room temperature and was stirred overnight. It was then neutralised with 2.5M HCl and extracted with ether. The extracts were washed with brine and dried over Na$_2$SO$_4$. After filtration of the drying agent and evaporation of the solvent, the residue was chromatographed on silica gel using ether:hexane (1:10) and then (1:5) as eluant. Two major components were isolated.

Component 1—0.16 g MH$^+$ 351

$v_{max}$ (liquid film) 3079, 3014, 1647 cm$^{-1}$ $^1$H NMR inconsistent with simple tetraallyl structure Component 2—1.16 g (36%) MH$^+$ 351

$v_{max}$ (liquid film) 3079, 3015, 1647 cm$^{-1}$ $\delta_H$(CDCl$_3$) 1.2–1.4 (1H,m, —CH$_A$H$_B$—), 1.95–2.05 (1H, m, —CH$_A$H$_B$—) 2.25–2.50 (4H,m, —CH-ring), 3.30–3.55 (8H,m, —CH—CH$_2$O—), 3.89–3.94 (8H,m, —OCH$_2$-allyl), 5.10–5.28 (8H,m,—CH=CH$_2$), 5.84–5.94 (4H,m, —CH=CH$_2$).

1.0 g of overlap of Components 1 and 2 was also recovered.

EXAMPLE 15

Preparation of 1,2,3,4-tetra (carbo-$^t$butoxymethoxymethyl) cyclopentane—Compound 15

To a suspension of 1,2,3,4-tetra(hydroxymethyl) cyclopentane (Cmpd. 6, 0.38 g, 2 mmol) and KOH (0.90 g, 16 mmol) in DMSO (2 ml) was added slowly t-butyl bromoacetate (3.90 g, 20 mmol) during 1 h at 0° C. The reaction mixture was stirred for an additional 2.5 h at 0° C. and the temperature was gradually increased to 10° C. during 2 h. The solid was removed by filtration through celite and was washed with CH$_2$Cl$_2$ several times. The filtrate was washed with water and brine, and was then dried over MgSO$_4$. After purification by column chromatography on silica gel eluted with hexane/EtOAc (3:1 to 1:1), the corresponding tetraester and the triester were obtained in 10% and 20% yields, respectively.

Tetraester $^1$H NMR (CDCl$_3$): 0.7–0.9 (m, 1H, —CH$_A$H$_B$—), 1.45 (s, 36H, $^t$Bu), 1.9–2.1 (m, 1H, —CH$_A$H$_B$—), 2.3–2.5 (m, 4H, ring), 3.4–3.7 (m, 8H, ring-CH$_2$O) and 3.91 (s, 8H, OCH$_2$COO)ppm, $^{13}$C NMR (CDCl$_3$): 28.1 (q, Me), 32.4 (t, —CH$_2$-in ring), 40.1 (d, —CH-ring), 42.9 (d, —CH-ring), 68.7 (t, OCH$_2$COO), 69.3 (t, ring-CH$_2$O), 73.0 (t, ring-CH$_2$O), 81.2 (s, COOC(CH$_3$)$_3$), 169.8 (s, COO) and 169.6 (s, COO) ppm.

Triestermono-OH (including isomers); $^1$H NMR (CDCl$_3$): 0.7–0.9 (m, 1H, —CH$_A$H$_B$—), 1.43 (s, 27H, $^t$Bu), 1.7–2.0 (m, 1H, —CH$_A$H$_B$—), 2.2–2.6 (m, 4H, —CH-ring), 3.0 (brs, 1H, OH), 3.4–3.7 (m, 8H, ring-CH$_2$O) and 3.8–4.0 (m, 6H, OCH$_2$COO) ppm; $^{13}$C NMR (CDCl$_3$): 28.1 (q), 30.3 (t), 31.7 (t), 38.8 (d), 39.2 (d), 40.7 (d), 42.4 (d) 43.0 (d) 43.2 (d), 44.1 (d), 46.7 (d), 60.2 (t), 63.4 (t), 68.9 (t), 69.0 (t), 69.3 (t), 69.4 (t), 72.6 (t), 72.9 (t), 73.0 (t), 81.4 (s), 81.7 (s), 81.9 (s), 169.4 (s) and 169.6 (s) ppm.

EXAMPLE 16

Preparation of 1,2,3,4-tetra (2'-N-benzyloxycarboxamido-ethoxymethyl)cyclopentane—compound 16

Carbonyl diimidazole (0.368 g, 2.27 mmol) was added slowly to 1,2,3,4-tetra(2'-carboxyethoxymethyl) cyclopentane (Cmpd. 13, 0.239 g, 0.5 mmol) at 0° C. CO$_2$ gas was evolved. After stirring at 0° C. for 1h, O-benzyl hydroxylamine hydrochloride (0.367 g, 2.3 mmol) and triethylamine (0.233 g, 2.3 mmol) were added to the solution at 0° C. The reaction mixture was stirred overnight (0° C. to room temperature). CH$_2$Cl$_2$ (50 ml) was added into the solution. The solution was washed with 1N HCl, brine and was the dried over MgSO$_4$. After purification by column chromatography on silica gel eluted with EtOAc/MeOH (19:1) and then EtOAc/Acetone/MeOH (10:9:1), the yield of product was 63%.

$^1$H NMR (CDCl$_3$): 1.1–1.3 (m, 1H, —CH$_A$H$_B$—, 1.6–1.8 (m, 1H, —CH$_A$H$_B$—), 2.07 (m, 4H, —CH-ring), 2.28 (m, 8H, CH$_2$CO), 3.1–3.4 (m, 8H —CH$_2$O—), 3.4–3.7 (m, 8H —CH$_2$O—), 4.64 (s, 8H, CH$_2$Ph), 7.1–7.2 (m, 20H, arom), 10.06 (brs, 2H, NH) and 10.19 (brs, 2H, NH) ppm; $^{13}$C NMR (CDCl$_3$): 31.6 (t, —CH$_2$ ring), 33.7 (d, CH$_2$CO), 40.0 (d ring), 42.6 (d, ring), 66.2 (t, OCH$_2$CH$_2$CO), 68.3 (t, —CH$_2$O), 71.8 (t, —CH$_2$O), 78.0 (t, CH$_2$Ph), 128.4 (d,arom), 129.0 (d,arom), 135.4 (s, arom) and 169.4 (s, COO) ppm; MS (FAB): 921 (MNa$^+$).

EXAMPLE 17

Preparation of 1,2,3,4-tetra (2'-N-hydroxy-carboxamidoethoxymethyl)cyclopentane—Compound 17

The tetra O-benzyl hydroxamate (Cmpd.16, 0.25 g, 0.28 mmol) was dissolved in a degassed 4.4% formic acid-methanol solution (20 ml) under nitrogen. The solution was added using a cannula to a suspension of palladium on activated carbon (200 mg) in a degassed 4.4% formic acid-methanol solution (20 ml) at room temperature. The reaction mixture was stirred at room temperature overnight under nitrogen. The catalyst was filtered off through celite. The solvent was removed by rotary evaporation. The product was dried under vacuum and its yield was 122 mg (81%). $^1$H NMR clearly showed that benzyl group was completely removed.

MS (FAB): 561 (MNa$^+$), 539 (MH$^+$)

EXAMPLE 18

Alkylation of cyclopentadienylsodium with methyl bromoacetate and subsequent trapping by maleic anhydride Preparation of cyclopentadienylsodium solution Dry toluene (10 ml) was added to sodium (1.5, 0.07 mmol) and the mixture was heated to reflux under a nitrogen atmosphere. When the sodium had melted the mixture was stirred rapidly for 15 min to produce a fine grained sodium sand. The heat source was removed and stirring was discontinued. The toluene was decanted from the sodium using a cannula and the sodium was washed with THF (3×10 ml). THF (20 ml) was then added and the mixture was cooled to −10° C. Cyclopenta-1,3-diene (5 ml, 0.06 mol) in THF (10 ml) was added dropwise so that hydrogen evolved slowly. When addition was complete the cooling bath was removed and the mixture was allowed to stir overnight. The colourless solution was then decanted off the excess unreacted sodium sand.

Alkylation

Methyl bromoacetate (5.07 ml, 0.055 mol) in THF (15 ml) was degassed and placed under a N$_2$ atmosphere. It was cooled to −78° C. using an acetone/dry ice bath. To this solution was added a solution of cyclopentadienylsodium in THF, prepared as above using sodium (1.5 g, 65 mmol) and cyclopenta-1,3-diene (4.5 ml, 55 mmol). The addition of the solution to methyl bromoacetate was carried out at −78° C. and the mixture was then allowed to stir overnight. The reaction mixture was allowed to warm to 0° C. Ether (30 ml, −5° C.) and water (25 ml, 0° C.) were added. The organic layer was washed rapidly with water (4×25 ml, 0° C.) and was dried over MgSO$_4$. The solvent was removed by rotary evaporation at −5° C. The residue was dissolved in toluene:ether (1:1) (20 ml, −5° C.) and was added dropwise to a suspension of maleic anhydride (5.36 g, 55 mmol) in toluene:ether (1:1) (50 ml) at −5° C. The reaction mixture was brought to room temperature slowly over 30 min. A white solid precipitated out. This was recrystallised from ethyl acetate.

Yield: 2.73 g (22%), m.p. 139°–141° C.

$\nu_{max}$ (KBr disc) 1859(m), 1779(s), 1728(s) cm$^{-1}$.

$\delta_H$ (CDCl$_3$) 2.45 (3H,m, —CHCHCH—), 3.45(2H,m, —CH$_2$—CO$_2$Me), 3.68 (5H,m, —CH—CO— and OCH$_3$), 6.27(2H,m, —CH=CH—).

EXAMPLE 19

Spectrophotometric titrations to determine the stability constant of gadolinium with the 1,2,3,4-tetra(2'-carboxyethoxymethyl)cyclopentane—Compound 13

An acetate buffer solution (0.01M NaOAc, pH=3.89, ionic strength=0.1) was prepared using NaOAc (0.4114 g) and NaCl (2.9233 g) in water (made up to 5000 ml) and adjusted to pH=3.89 by addition of acetic acid.

A solution of the ligand was prepared by making the tetraacid compound 13 (3.43 mg) up to 25 ml with buffer solution and then diluting 1 ml of this solution to 25 ml with buffer to give a ligand concentration of 1.47×10$^{-5}$M.

A Gd-Arsenazo III complex solution was prepared such that [Gd]=1.1924×10$^{-5}$M and [ArIII]=7.391×10$^{-5}$M using gadolinium chloride and Arsenazo III diluted with buffer solution.

The stability constant of gadolinium with the ligand was measured by titrating a solution at the Gd-arsenazo III mixture with the ligand. 2.5 ml of the Gd-ArIII solution was transferred into 11 tubes, 0.1, 0.2, 0.3, 0.4, 0.5, 0.6, 0.7, 0.8, 0.9, 1.0 and 2.0 ml of the ligand solution was added to each tube. The tubes were sealed and were heated to 60° C. overnight. They were then cooled to room temperature and the UV spectrum of each was recorded. Using the program described in the literature$^{(9)}$ the stability constant for the gadolinium-tetraacid was calculated to be log K$_a$=21.

STRUCTURES OF COMPOUNDS

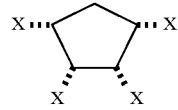

| | |
|---|---|
| Compound 1 | X = CO$_2$H |
| Compound 2 | X = CO$_2$Et |
| Compound 3 | X = CO$_2$Me |
| Compound 4 | X = CONHCH$_2$Ph |
| Compound 5 | X = CON(CH$_2$Ph)CH$_2$CH=CH$_2$ |
| Compound 6 | X = CH$_2$OH |
| Compound 7 | X = CH$_2$OMs |
| Compound 8 | X = CH$_2$SCH$_2$CO$_2$Me |
| Compound 9 | 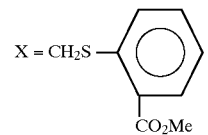 |
| | X = CH$_2$S— |
| Compound 10 | X = CH$_2$OCH$_2$CH$_2$CN |
| Compound 11 | X = CH$_2$OCH$_2$CH$_2$CO$_2$Me |
| Compound 12 | X = CH$_2$OCH$_2$CH$_2$CO$_2$$^t$Bu |
| Compound 13 | X = CH$_2$OCH$_2$CH$_2$CO$_2$H |
| Compound 14 | X = CH$_2$OCH$_2$CH=CH$_2$ |
| Compound 15 | X = CH$_2$OCH$_2$CO$_2$$^t$Bu |
| Compound 16 | X = CH$_2$OCH$_2$CH$_2$CONHOCH$_2$Ph |
| Compound 17 | X = CH$_2$OCH$_2$CH$_2$CONHOH |

REFERENCES

1. K. Alder, J. H. Moells and R. Reeber. *J.Liebigs.Ann.Chem.* 1958, 611, 7–32.
2. W. H. Edgerton. U.S. Pat. No. 3,723,526.
3. R. van Volkenburg. U.S. Pat. No. 3,507,894.
4. Bridge Chemical Ltd. Fr. 1,447,835 (California 66:46138s).
5. P. Haas and H. Hettel, U.S. Pat. No. 4,493,909.
6. G. Seitz, H. Hoffmann and G. Kroemeke. *Arch.Pharm.,* 309, 44 (1976).
7. L. M. Tolbert, J. C. Gregory and C. P. Brock. *J.Org.Chem.,* 50, 548 (1985).
8. idem. *Acta.Cryst.Sect.C,* C42 1063 (1986).
9. G. Seitz and G. Kroemeke, *Arch.Pharma.,* 309, 930 (1976).
10. H. Bohme and G. Seitz. *Chem.Ber.* 1968, 101, 1689.
11. E. T. Clarke and A. E. Martell. *Inorg.Chimica.Acta.* 1991, 190, 27–36, 37–46.
12. C. J. Broan, J. P. L. Cox, A. S. Craig, R. Kataky, D. Parker, A. Harrison, A. M. Randall and G. Ferguson. *J.Chem.Soc.Perkin.Trans.*2, 1991, 87.
13. C. A. Chang and M. E. Rowland. *Inorg.Chem.* 1983, 22, 3866.
14. W. P. Cacheris, S. K. Nickle and A. D. Sherry. *Inorg.Chem.* 1987, 26, 958.
15. A. D. Sherry, R. D. Brown, C. F. G. C. Geraldes et al. *Inorg.Chem.* 1989, 28, 620.
16. U. Krueger and H. Rupp, WO 91/10454.

17 W. Schneider, I. Erni and H. K. Hegetschweiler, U.S. Pat. No. 4,794,197 and WO 92/04056.
18 E. J. Corey, U. Koelliker and J. Neuffer. *J.Amer.Chem.Soc.* 1971, 93, 1489.
19 E. J. Corey, N. M. Weinshenker, T. K. Schaaf and W. Huber. *J.Amer.Chem.Soc.* 1969, 91, 5675.
20 Janssen Chimica Catalogue No. 11 150 92.2
21 R. P. Mariella and R. A. Blau. *Can.J.Chem.* 1967, 45(1), 85.

We claim:

1. Substituted cyclopentane compounds of the formula

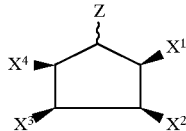

wherein $X^1$, $X^2$, $X^3$ and $X^4$ may be the same or different and each is selected from the group consisting of —CONRR$^1$, —CH$_2$NHCOR, —CH$_2$OCOR, —CH$_2$OR$^1$, —CH$_2$SR$^1$, —CH$_2$SOR, —CH$_2$SO$_2$R or —CH$_2$SO$_2$NRR$^1$, R may be the same or different and each is a C1–C12 hydrocarbon which is optionally substituted with a ligand donor group or a group which permits attachment to a biologically active molecule or insoluble support, $R^1$ is H or R, Z is hydrogen or C1–C20 hydrocarbon which is optionally substituted with a group which permits attachment to a biologically active molecule or insoluble support, provided that when each of $X^1$, $X^2$, $X^3$ and $X^4$ is CH$_2$OR$^1$, then $R^1$ includes a ligand donor group, provided that, when each of $X^1$, $X^2$, $X^3$ and $X^4$ is —CONRR$^1$, then R and $R^1$ are not both $C_{2-6}$ mono- or di-hydroxyalkyl and Z is not H, and provided that at least one of R, $R^1$ and Z contain a ligand donor group or a group which permits attachment to a biologically active molecule or insoluble support.

2. Compounds as claimed in claim 1, wherein R includes a ligand donor group selected from the group consisting of those derived from O—, N—, and S-containing heterocycles, thiols, thioethers, ethers, amines, nitriles, alcohols, ketones and carboxylic, phosphonic, phosphinic, boronic, sulphonic, arsonic and arsinic acids and their amides and esters, β-diketones, Schiff bases, α-hydroxycarboxylic acids, α-ketocarboxylic acids and hydroxamic acid.

3. Compounds as claimed in claim 1, which are attached through Z or a group R to a biologically active molecule or insoluble support.

4. Compounds as claimed in claim 1, wherein all four groups X are the same.

5. Compounds as claimed in claim 1, which are octadentate ligands.

6. Compounds as claimed in claim 1, wherein each of $X^1$, $X^2$, $X^3$ and $X^4$ is —CH$_2$OR or —CH$_2$SR and each R is carboxyethyl or lower alkyl carboxyethyl or cyanoethyl or alkyl.

7. Cis,cis,cis-1,2,3,4-tetra(cyanoethoxymethyl) cyclopentane.

8. 1,2,3,4-tetra(2-carboxyethoxymethyl) cyclopentane.

9. The complex of the compound as claimed in claim 1, with an alkaline earth or transition or lanthanide or actinide metal ion.

10. The complex of the compound as claimed in claim 9, with an alkaline earth or transition or lanthanide or actinide metal ion.

11. The complex of the compound as claimed in claim 8, with an alkaline earth or transition or lanthanide or actinide metal ion.

* * * * *